US00PP25629P2

(12) United States Plant Patent
Mikósné

(10) Patent No.: US PP25,629 P2
(45) Date of Patent: Jun. 23, 2015

(54) ***PRUNUS* PLANT NAMED 'NERO'**

(50) Latin Name: *Prunus laurocerasus*
Varietal Denomination: Nero

(71) Applicant: Józsa Mikósné, Szombathely (HU)

(72) Inventor: Józsa Mikósné, Szombathely (HU)

( * ) Notice: Subject to any disclaimer, the term of this patent is extended or adjusted under 35 U.S.C. 154(b) by 177 days.

(21) Appl. No.: 13/986,512

(22) Filed: May 9, 2013

Related U.S. Application Data

(60) Provisional application No. 61/797,652, filed on Dec. 12, 2012.

(51) Int. Cl.
*A01H 5/12* (2006.01)

(52) U.S. Cl.
USPC ..... Plt./180

(58) Field of Classification Search
USPC ..... Plt./180
See application file for complete search history.

*Primary Examiner* — Anne Grunberg
(74) *Attorney, Agent, or Firm* — Penny J. Aguirre

(57) ABSTRACT

A new cultivar of *Prunus laurocerasus*, 'Nero', characterized by its elongated dark green glossy mature leaves and young leaves that are yellow-green, bushy spreading mounded plant habit; reaching about 2 m in height and 3 m in width, its moderate growth rate, its good disease resistance, and its hardiness at least in U.S.D.A. Zones 6 to 9.

2 Drawing Sheets

Botanical classification: *Prunus laurocerasus.*
Variety denomination: 'Nero'.

BACKGROUND OF THE INVENTION

The present invention relates to a new and distinct cultivar of *Prunus laurocerasus*, and will be referred to hereafter by its cultivar name, 'Nero'. 'Nero' is a new cultivar of cherry laurel grown for use as a landscape plant.

The new cultivar of *Prunus*, 'Nero', arose from an ongoing breeding program by the Inventor in Szombathely, Hungary. The new cultivar was selected as a naturally occurring whole plant mutation in summer of 2002 that arose from seeds collected, pooled and sown from open pollination of the cultivars 'Mari', 'Piri', and Klàri (all three not patented). The exact parenage is unknown.

Asexual propagation of the new cultivar was first accomplished by stem cuttings by the Inventor in Szombathely, Hungary in September of 2007. Asexual propagation by stem cuttings has determined that the characteristics of the new cultivar are stable and reproduced true to type in successive generations.

SUMMARY OF THE INVENTION

The following traits have been repeatedly observed and represent the characteristics of the new *Prunus*. These attributes in combination distinguish 'Nero' as a unique cultivar of *Prunus*.

1. 'Nero' exhibits elongated dark green glossy mature leaves and young leaves that are bronze-yellow.
2. 'Nero' exhibits a bushy spreading mounded plant habit; reaching about 2 m in height and 3 m in width.
3. 'Nero' exhibits a moderate growth rate.
4. 'Nero' exhibits good disease resistance.
5. 'Nero' exhibits good hardiness with hardiness at least in U.S.D.A. Zones 6 to 9.

'Nero' is unique and unlike any other cultivars of *Prunus laurocerasus* known to the Inventor. Possible parent plants;

'Mari', 'Piri', and Klàri, all differ from 'Nero' in lacking glossy leaves, and in having leaves that are less elongated. 'Nero' an be most closely compared to the cultivars 'Caucasica' (not patented) and 'Otto Luyken' (not patented). 'Caucasica' is similar to 'Nero' in foliage coloration, however 'Caucasica' differs from 'Nero' in having leaves that are less elongated and in having a more vigorous growth habit. 'Otto Luyken' is similar to 'Nero' in having glossy dark green mature leaves, but differs from 'Nero' in having a plant habit that is less dense and in not being as realiably cold hardy when grown under the same conditions.

BRIEF DESCRIPTION OF THE DRAWING

The accompanying colored photographs illustrate the overall appearance and distinct characteristics of the new cultivar. The photographs were taken of 6 year-old plants as grown outdoors in a trial bed in Szombathely, Hungary.

The photograph in FIG. 1 illustrates the plant habit of 'Nero'.

Figure 1:
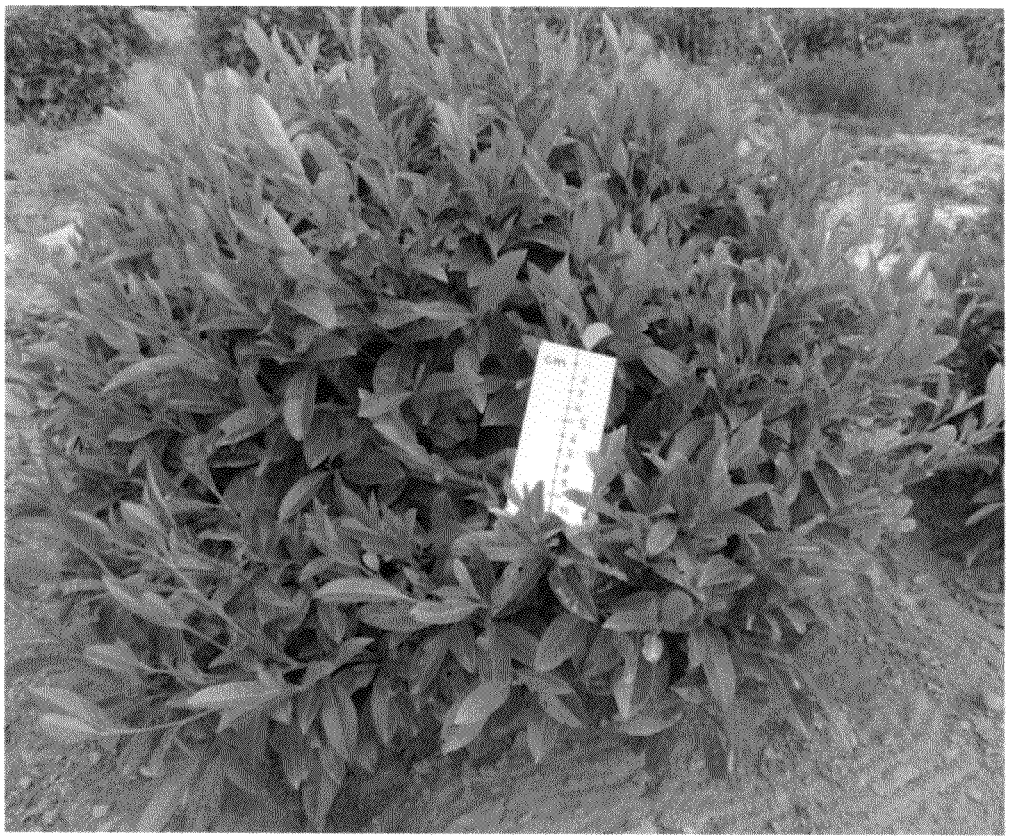
Figure 2:
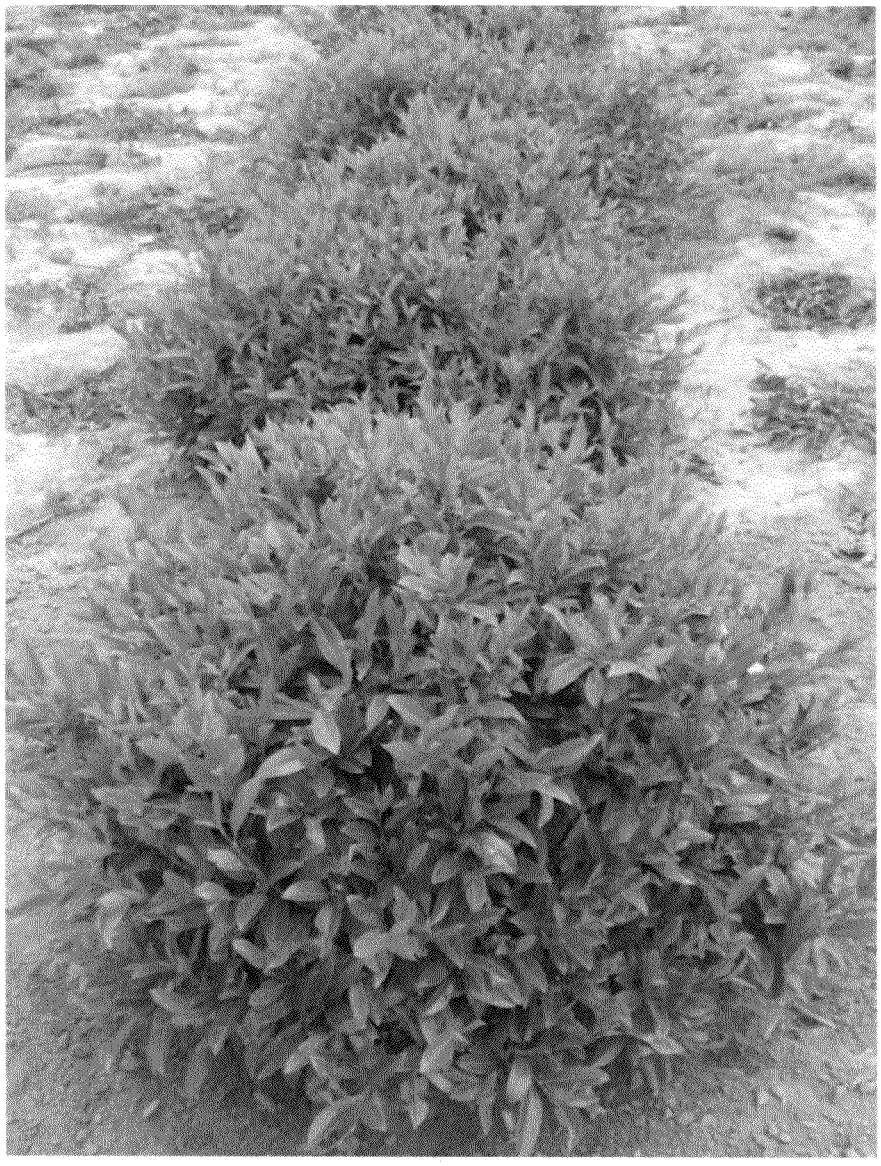

The photograph in FIG. 2 is a view of a row of plants of 'Nero'.

The colors in the photographs are as close as possible with the digital photography techniques available, the color values cited in the detailed botanical description accurately describe the colors of the *Prunus.*

DETAILED BOTANICAL DESCRIPTION

The following is a detailed description of 6 year-old trees of the new cultivar as grown outdoors in a trial bed in Szombathely, Hungary. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Plant type.*—Evergreen shrub.
*Plant habit.*—Spreading and mounded.
*Height and spread.*—Reaches about 2 m in height and about 3 m in width.
*Hardiness.*—At least in U.S.D.A. Zones 6 to 9.
*Diseases and pests.*—Has been shown to have good resistance to powdery mildew and leaf spot.
*Root description.*—Fleshy.
*Propagation.*—Stem cuttings.
*Root initiation.*—4 to 6 weeks in a greenhouse at 16 to 20° C. in autumn.
*Root development.*—Autumn rooted cuttings are over-wintered in a cool greenhouse and planted in liners in the spring that fully develop in 45 days at 20° to 25° C.
*Growth rate.*—Moderate.

Stem description:
*Shape.*—Slightly oval.
*Stem color.*—New growth; 144D, mature growth; 144B, mature wood; N199B.
*Branching.*—10 to 12 main stems and 25 to 30 lateral branches per main stem with an average angle of 45°.
*Stem size.*—Main stems; 0.5 to 0.6 m in length and an average of 1.5 cm in diameter, lateral branches range from 15 to 20 cm in length and an average of 0.5 cm in diameter.
*Stem surface.*—Young stems glabrous with slight glossy, mature stems dull.
*Branch internode length.*—Average of 2 to 3 cm.
*Stem fragrance.*—Emit a cherry aroma if bruised.

Foliage description:
*Leaf shape.*—Oblong.
*Leaf division.*—Simple.
*Leaf base.*—Cuneate.
*Leaf apex.*—Acute to cuspidate.
*Leaf fragrance.*—None.
*Leaf venation.*—Pinnate, conspicuously recessed on upper surface, color on mature leaves upper and lower surface is 145B to 145C.
*Leaf margins.*—Entire.
*Leaf arrangement.*—Alternate.
*Leaf attachment.*—Petiolate.
*Leaf surface.*—Glabrous and highly glossy on upper and flightly glossy on lower surface.
*Leaf size.*—Mature leaves average 6 to 7 cm in length and 1.5 to 2 cm in width.
*Leaf internodes.*—2 to 3 cm.
*Leaf color.*—Newly expanded leaves upper and lower surface; a blend of 154C and 164B, mature leaves upper and lower surface is 137B.
*Petioles.*—Average of 0.5 cm in length and 2 mm in width, green in color, glabrous surface.

Inflorescence description: Blooms have not been observed on the new cultivar.

It is claimed:

1. A new and distinct cultivar of *Prunus* plant named 'Nero' as herein illustrated and described.

* * * * *

UNITED STATES PATENT AND TRADEMARK OFFICE

CERTIFICATE OF CORRECTION

PATENT NO. : PP25,629 P2
APPLICATION NO. : 13/986512
DATED : June 23, 2015
INVENTOR(S) : Józsa Miklósné

It is certified that error appears in the above-identified patent and that said Letters Patent is hereby corrected as shown below:

On the title page item 12, item 71 and item 72

Please change the name of the inventor in the appropriate location

Józsa Mikósné TO Józsa Miklósné

Signed and Sealed this
First Day of March, 2016

Michelle K. Lee

Michelle K. Lee
*Director of the United States Patent and Trademark Office*